July 1, 1958 E. H. SCANLON Plant Pat. 1,722
CONICAL OR PYRAMIDAL RED MAPLE TREE
Filed May 23, 1957
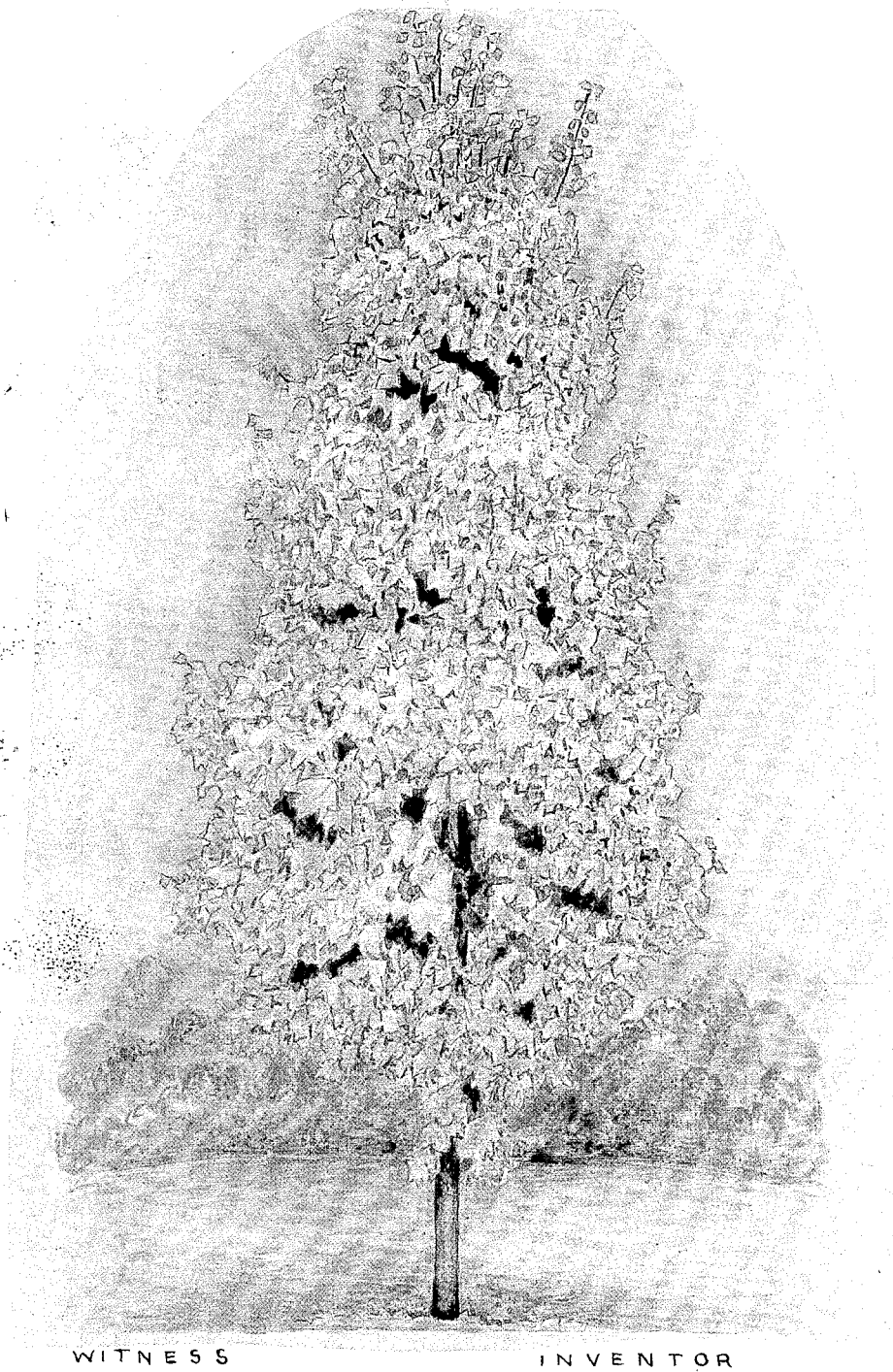
WITNESS
Addison E Avery
INVENTOR
EDWARD H. SCANLON
By: Golrick & Golrick
ATTYS.

United States Patent Office

Plant Pat. 1,722
Patented July 1, 1958

1,722

CONICAL OR PYRAMIDAL RED MAPLE TREE

Edward H. Scanlon, Olmsted Falls, Ohio

Application May 23, 1957, Serial No. 661,269

1 Claim. (Cl. 47—59)

This invention or discovery relates to a new and distinct variety of conical red maple tree, characterized in addition to its functional form, by the proclivity of imparting uniform fall colors of red and yellow to the clone. This coloring characteristic has been established after nine years of growing and observation.

This variety of red maple tree as a shade or ornamental tree has decided advantages for street planting particularly in closely built urban areas. As a pyramidal, or more accurately, conical type tree of elongated form, a good bottom spread for shade and appearance is obtained; while narrow top growth minimizes not only storm hazards and damage to the tree itself, and to nearby persons and property in consequence of broken or falling limbs, but also tree damage repair and normal tree maintenance labor and problems. For similar reasons the upsweeping branches with strong crotches are also advantageous in urban environment.

With respect to ornamental characteristics in addition to the aforementioned features of shape, the tree has a relatively dense summer growth of large lustrous green leaves, which turn in fall to an intense vivid coloration in the red to yellow range, as hereinafter characterized, that is quite uniform not only throughout the individual tree, but from tree to tree in a given area of planting. Further it has been found that the fall color is consistently retained with trees of this variety planted in areas widely diverse geographically, climatically and environmentally, even in soils differing greatly in structure, pH and general chemical constitution.

This new variety originated in scion stock taken from a red maple parent of pleasing form, and the fall color characteristic above described was first noted in clonal propagules derived from such stock. Said stock comprised two scions which, engrafted on separate root stock, resulted in two trees of identical characteristics. Asexual reproduction over nine years has now clearly shown that the ability to achieve the fall color characteristic has been retained, and also the well defined conical shape.

The most outstanding characteristic, of great ornamental value, whereby this clone is distinguished from other varieties of red maples is the fall color characteristic as set forth; although the elongated or relatively narrow base conical growth is also a distinctive point.

In the drawings, there is shown the form and fall color of a tree of the new variety.

Characters identifying this new variety as a variant of *Acer rubrum*, and not of any other species of maple, include the marked glaucescence on the dorsal surface of the leaves, the leaf sinuses acutely V-shaped and not extending more than halfway to base, the leaf lobes apiculately double-serrate, and the samaras glabrous when young, 1.5–2.5 cm. long with wings forming a V-shaped sinus. It differs from other known varieties of red maple (*Acer rubrum*) by characters given in the following description.

The new variety is a uniformly narrow-conical (narrow pyramidal) tree in habit, the upper branches progressively shorter than those beneath them and becoming increasingly ascending in habit as the apex is approached. Whereas typical *Acer rubrum* and known preexisting varieties are characterized in part by an uneven autumn coloration varying with site, season, and region, and in colors ranging from orange-red to dark crimson, the autumn coloration of clonal propagules of the instant variety display autumn color constancy not known to be modified by site or region, and identified as varying between the rather narrow limits of bright orange-umber and bright orange-scarlet, as designated in the "Royal Horticultural Society Color Chart," sometimes known as the "Wilson Chart."

This new variety has been asexually reproduced by budding at Olmsted Falls, Ohio.

I claim:

A new and distinct variety of red maple tree as described and illustrated characterized by its elongated conical form and particularly by its autumn coloration and constancy thereof.

No references cited.